United States Patent [19]

Caldow et al.

[11] Patent Number: 5,118,959
[45] Date of Patent: Jun. 2, 1992

[54] WATER SEPARATION SYSTEM FOR CONDENSATION PARTICLE COUNTER

[75] Inventors: Robert Caldow, Minneapolis; Veryl L. Denler, Bethel, both of Minn.

[73] Assignee: TSI Incorporated, St. Paul, Minn.

[21] Appl. No.: 695,265

[22] Filed: May 3, 1991

[51] Int. Cl.⁵ .................................. G01N 15/06
[52] U.S. Cl. .................................. 250/573; 356/37
[58] Field of Search ............... 250/573; 356/37, 335, 356/336

[56] References Cited

U.S. PATENT DOCUMENTS

| | | |
|---|---|---|
| 3,694,085 | 9/1972 | Rich . |
| 3,806,248 | 4/1974 | Sinclair . |
| 4,449,816 | 5/1984 | Kohsaka et al. . |
| 4,790,650 | 12/1988 | Keady . |
| 5,026,155 | 6/1991 | Ockovic et al. ............... 356/37 |

OTHER PUBLICATIONS

2nd International Aerosol Conference, Berlin © 1986 Pergamon Journals Ltd., Printed in Great Britain, M. R. Stoizenburg et al., "Counting Efficiency of An Ultrafine Aerosol Condensation Nucleus Counter: Theory and Experiment", pp. 786-789.

Primary Examiner—David C. Nelms
Assistant Examiner—Khaled Shami
Attorney, Agent, or Firm—Haugen and Nikolai

[57] ABSTRACT

A continuous flow condensation particle counter employs a working fluid to saturate a gas stream, and then condense onto particles carried in the gas stream as the stream is directed through a condenser and cooled below the supersaturation point. A porous saturation block is positioned beneath the condenser, and receives droplets of working fluid condensate and water as the droplets descend from the condenser by gravity. The saturation block is constructed of a hydrophobic material, whereby it allows the working fluid to pass through but retains water within a collection reservoir centered below the condenser. A vacuum pump and a periodically actuated solenoid valve are employed to introduce a partial vacuum to the reservoir and thereby evacuate accumulated water. The preferred working fluid is a perfluorinated hydrocarbon fluid that is substantially odorless, chemically inert and non-flammable. Water is immiscible in the working fluid, and thus readily separable.

21 Claims, 2 Drawing Sheets

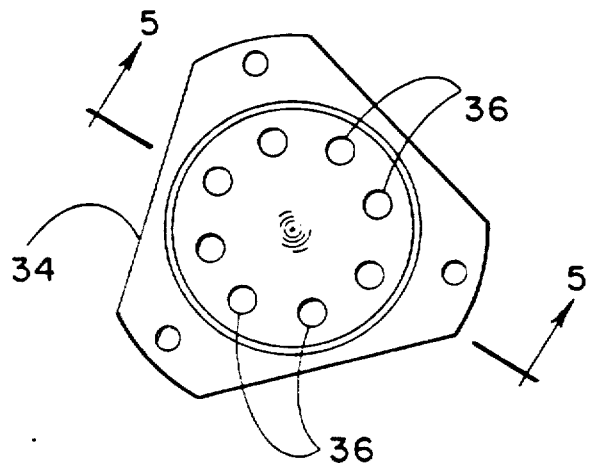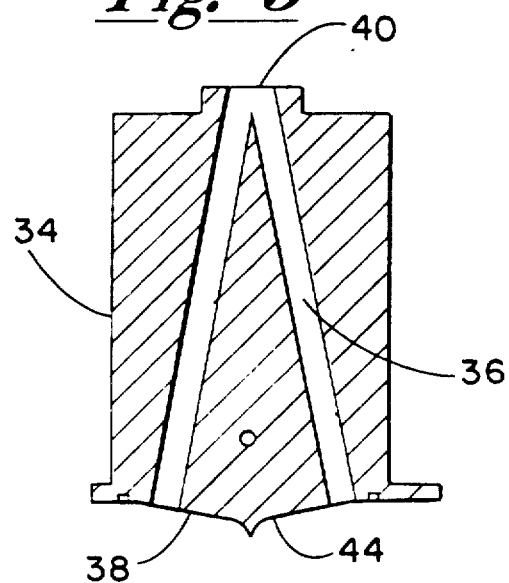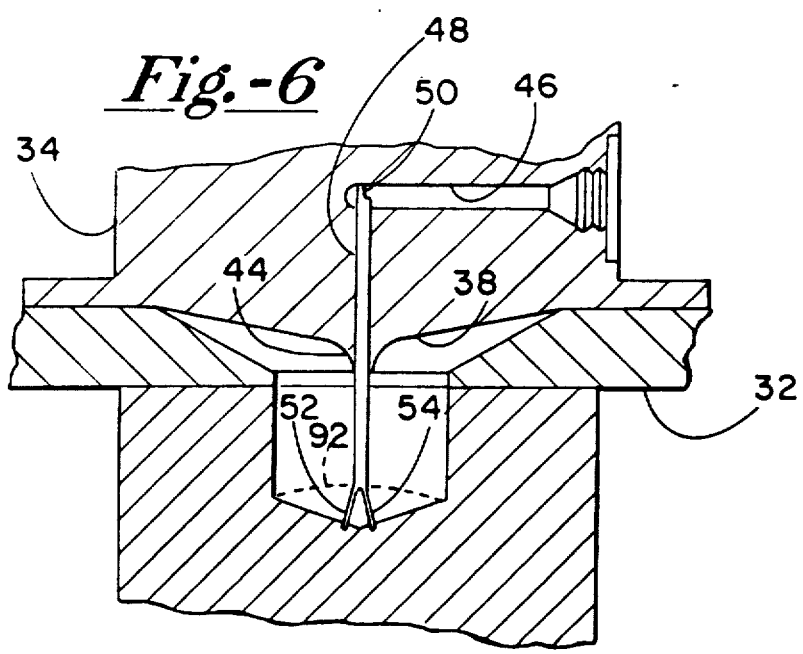

WATER SEPARATION SYSTEM FOR CONDENSATION PARTICLE COUNTER

BACKGROUND OF THE INVENTION

The present invention relates to instruments that measure the concentration of fine particles in gas, known as condensation nuclei counters or condensation particle counters. More particularly, the invention concerns a condensation particle counter using a water-immiscible working fluid, and a means for removing water from the working fluid.

For years, condensation particle counters have been used successfully in aerosol research. More recently they have gained acceptance in industrial settings that require detecting fine and ultrafine airborne particles. In "clean rooms" used for the production of semi-conductor chips, disk drives, optical systems and pharmaceuticals, there is an increasing need to detect and measure concentrations of submicrometer particles.

Condensation particle counters operate according to the principle that supersaturated vapor condenses on fine particles to form aerosol droplets. Typically, room air (or other gas being monitored) is drawn through a horizontal chamber inside a saturator block. A working fluid, usually n-butyl alcohol (butanol), evaporates into the gas stream, saturating the stream with alcohol vapor. From the saturator, the gas is drawn into a vertical condenser tube and cooled sufficiently to supersaturate the vapor. Vapor condenses onto the particles, forming aerosol droplets much larger than the particles. From the condenser, the gas stream passes an optical detector that senses the aerosol droplets traveling through a viewing volume defined by a laser and associated optics. For further information on this type of device, reference is made to U.S. Pat. No. 4,790,650 (Keady), assigned to the assignee of this application.

When a continuous flow condensation particle counter is used to monitor room air, the air stream incorporates water vapor as well as working fluid vapor, and the condenser forms water as well as working fluid condensate. Over extended operation of the counter, increasing amounts of water are absorbed by the butanol. As the water concentration increases, instrument performance is degraded. Accordingly, it is necessary to periodically drain the butanol and water mixture from the device, and add pure butanol. The required frequency of working fluid replacement depends on the relative humidity of the air, but relative humidity levels of thirty percent or more can give rise to substantial fluid degradation. Further problems arise from the chemically reactive nature, flammability and disagreeable odor of butanol.

Therefore, it is an object of the present invention to provide a continuous flow condensation particle counter incorporating means for substantially preventing the introduction of water into the working fluid as the working fluid is recirculated through the particle counter.

Another object is to provide, in a condensation particle counter, a non-toxic, non-flammable and chemically inert working fluid in which water is immiscible.

A further object of the invention is to provide a simple and reliable system for collecting and removing water formed in a condensation particle counter.

Yet another object is to provide a continuous flow condensation particle counter particularly well suited for long term, low maintenance operation in high humidity environments.

SUMMARY OF THE INVENTION

To achieve these and other objects, there is provided a continuous flow condensation apparatus for detecting fine particles in a gas stream. The apparatus includes a moving means for drawing a sample gas in a stream along a path, with the sample gas containing fine particles and water vapor. The apparatus includes a fluid source providing a working fluid in which water is immiscible, the working fluid being in liquid form. A saturation means, along the path and in fluid communication with the fluid source, provides the working fluid to the gas stream for entrainment of the working fluid into the stream as a fluid vapor. A cooling means is disposed along the path downstream of the saturation means, and has a cooling surface exposed to the gas stream. The cooling means cools the gas stream below the supersaturation points of the fluid vapor and the water vapor, which causes the fluid vapor to condense onto the particles to form aerosol droplets. Also due to the cooling, working fluid condensate and water form on the cooling surface. A sensing means, downstream of the cooling means, defines a viewing volume that intersects the path, for detecting the droplets carried through the viewing volume by the sample gas. A separating means, proximate the condenser, receives the working fluid condensate and the water from the cooling surface. The separating means returns the working fluid condensate to the fluid source while retaining the water to prevent the water from reaching the fluid source.

Preferably the apparatus further includes a collecting means that gathers the water retained by the separating means, and an evacuation means in fluid communication with the collecting means, for removing the water gathered by the collecting means. For example, the separating means can include a porous structure formed of a hydrophobic material such as polypropylene, positioned directly beneath the cooling means to receive working fluid condensate and water by gravity. Then, a convenient collecting means is a depression in the separating structure, in the shape of a downwardly converging cone open to the top of the separating structure. In one advantageous arrangement, a porous saturation block is constructed of sintered polypropylene impregnated with carbon, and also functions as the separation means. The saturation body is partially submerged in a reservoir of the working fluid, and allows working fluid condensate to flow through to the reservoir, while capturing water in the reservoir.

Accumulated water is periodically removed from the reservoir by a vacuum pump also used to draw the gas stream through the particle counter and provide a purge air flow through the counter. More particularly, a valve is periodically actuated to place the vacuum pump in fluid communication with the reservoir, to draw water away from the reservoir through a capillary tube extending from the bottom of the reservoir to the cooling means.

Another aspect of the present invention is a process for detecting fine particles in a gas stream. The process includes the steps of:

directing a stream of gas containing water vapor through a saturation means to substantially saturate the gas with a working fluid;

directing the gas stream past a condenser, supersaturating the working fluid and the water vapor to cause the working fluid to condense onto each of the particles, to form a condensate of the working fluid along a condensing surface of the condenser, and to form water along the condensing surface;

collecting the working fluid condensate and the water at a designated collection area; and returning the working fluid from the collection area to the saturation means, while retaining the water to prevent it from reaching the saturation means.

Thus in accordance with the present invention, a continuous flow condensation particle counter can accurately determine particulate concentration, under high humidity conditions, with low maintenance and no need to periodically drain and replace the working fluid. The water-immiscible working fluid is chemically inert, non-toxic, and does not have the unpleasant odor of n-butyl alcohol, the conventional working fluid in these instruments. Separation and periodic removal of the water eliminates the degradation encountered in previous devices when water dilutes the working fluid, and reduces the exposure to water and any corrosion occasioned by such exposure.

IN THE DRAWINGS

For a further appreciation of the above and other features and advantages, reference is made to the following detailed description and to the drawings, in which:

FIG. 4 is a bottom view of the condenser;

FIG. 5 is a sectional view taken along the line 5—5 in FIG. 4; and

FIG. 6 is an enlarged view of a portion of FIG. 1.

DETAILED DESCRIPTION OF THE PREFERRED EMBODIMENT

Figure 1:
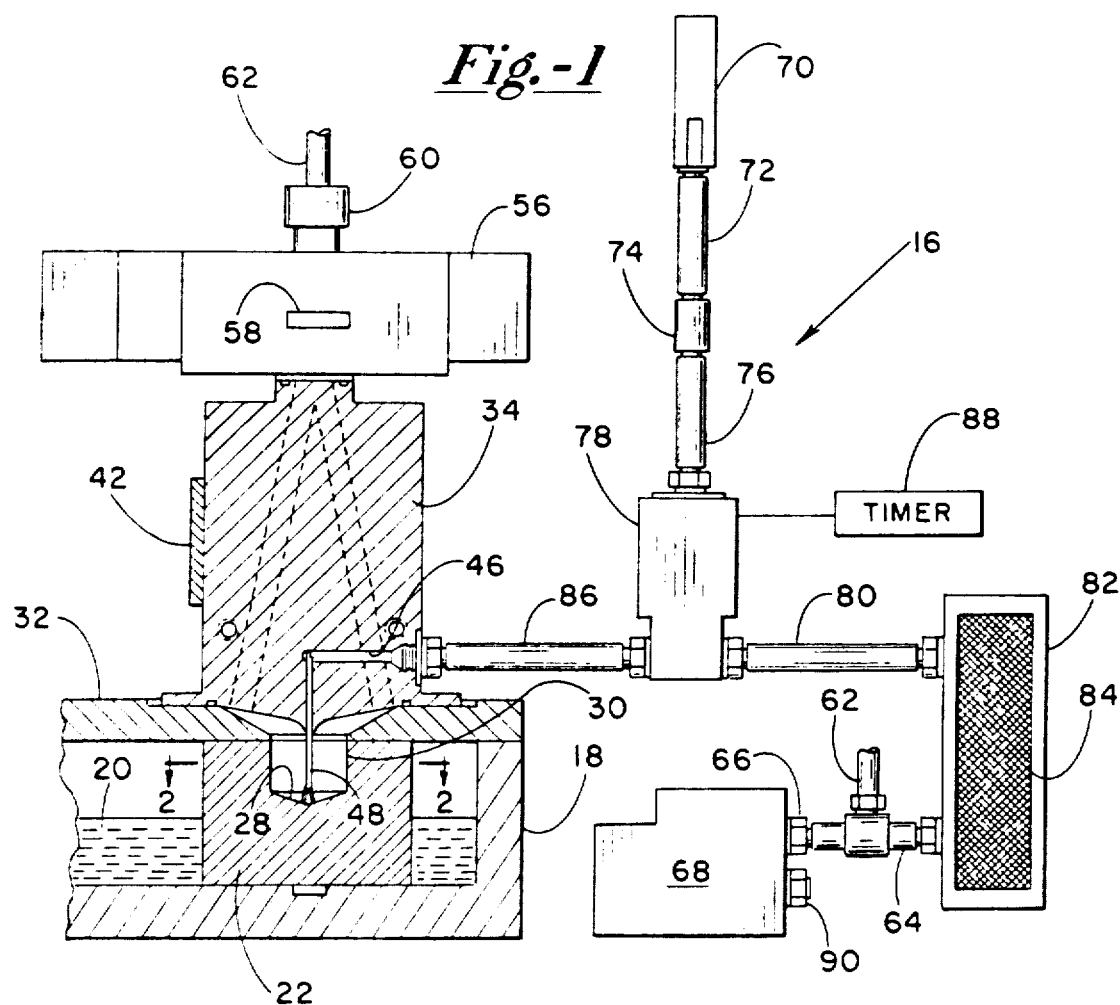
FIG. 1 is a schematic view partially in section of a condensation particle counter constructed in accordance with the present invention.

Turning now to the drawings, there is shown schematically in FIG. 1 a continuous flow condensation particle counter 16. The particle counter monitors airborne contamination by detecting particles as small as 0.02 micrometers in diameter. Such monitoring is critical in environments that must be substantially free from particulate contamination even at the submicron level, for example clean rooms used in producing semi-conductor chips. Particle counter 16 is illustrated schematically in FIG. 1, to emphasize certain features of the present invention. Further details on this type of instrument are found in the aforementioned U.S. Pat. No. 4,790,650, incorporated herein by reference.

Particle counter 16 includes a fluid reservoir 18 formed of anodized aluminum and containing a working fluid 20 in liquid form. The preferred working fluid is a perfluorinated hydrocarbon fluid available from Air Products and Chemicals Inc. (Allentown, Penna.) under the brand name APF-175. Working fluid 20 is odorless, non-toxic, non-flammable and substantially chemically inert, and accordingly is well suited for use in condensation particle counter 16. Water is immiscible in working fluid 20, facilitating separation of water from the fluid.

Figure 2:
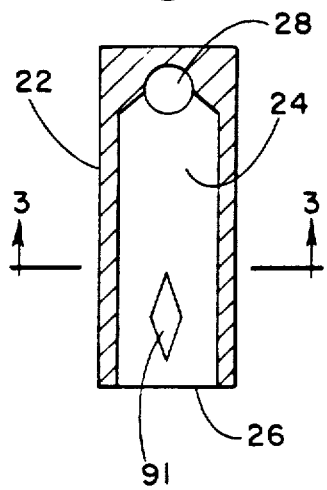
FIG. 2 is a sectional view taken along the line 2—2 in FIG. 1.
Figure 3:
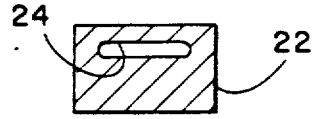
FIG. 3 is a sectional view taken along the line 3—3 in FIG. 2.

A saturation block 22 rests in reservoir 18, partially submerged in the working fluid. The saturation block is a rigid, highly porous body formed of hydrophobic material, preferably molded polyethylene, impregnated with carbon black to enhance its electrical conductivity. As best seen in FIGS. 2 and 3, an elongate horizontal opening is formed through the majority of the saturation block above the level of working fluid, to provide a saturation chamber 24. Chamber 24 is rounded along opposite side edges, and has a horizontal width substantially greater than its height to increase the ratio of surface area to chamber volume, thus to enhance saturation of air (or another gas) traveling through the chamber. Saturation block 24, by a wicking action, draws working fluid 20 upwardly and about the chamber, where it is entrained into the air stream in the form of a working fluid vapor.

From an inlet 26, chamber 24 is uniform in transverse profile until converging to a conical depression or collection reservoir 28. As seen in FIG. 1, a circular opening 30 is formed in saturation block 22 above and concentric with reservoir 28, whereby air flows upwardly as it leaves the saturation block.

Fluid reservoir 18 is enclosed by a top cover 32 formed of Delrin (brand name) acetal resin or another suitably hard polymeric material. An upwardly diverging truncated conical opening is formed through cover 32, concentric with collection reservoir 28 and opening 30.

A condenser 34, constructed of anodized aluminum, is mounted on cover 32. The cover supports the condenser directly above saturation block 22 and concentric with reservoir 28, and thermally isolates the condenser. Eight passages 36 extend upwardly from a bottom surface 38 of the condenser. More particularly, the openings are inclined from the vertical to converge at a common apex region 40 at the top of the condenser (FIG. 5). The circular interior walls of the passages, in combination with bottom surface 38, provide a cooling surface of the condenser exposed to the air stream. A thermoelectric heat pump 42 cools condenser 34, the condenser in turn cooling the air or gas stream.

As perhaps best seen in FIG. 6, the majority of bottom surface 38 is gradually inclined downwardly and radially inward. The bottom surface also is rounded at the inlet ends of passages 36. At the center of the condenser, however, the bottom surface is more steeply inclined to form a relatively steep projection 44 centered over reservoir 28.

A horizontal passageway 46 extends from the condenser exterior, radially inward between an adjacent pair of passages 36, to the center of the condenser. An upright capillary tube 48, formed of stainless steel, is mounted into condenser 34 at its center, extending from projection 44 upwardly and into passageway 46. A cutout 50 at the upper end of the tube insures that an elongate fluid passage through the tube is in fluid communication with passageway 46. The bottom portion of tube 48 extends downwardly from projection 44 into reservoir 28. At the bottom, tube 48 is split and opposing portions bent to form two inclined legs 52 and 54. The legs are embedded into saturation block 22 near the bottom of the collection reservoir, tending to stabilize the tube relative to the saturator and condenser, and protecting the tube from damage, particularly to the legs. The opening between legs 50 and 52 places the interior of tube 48 in fluid communication with reservoir 28.

Upon leaving condenser 34, the air enters an optical detection assembly 56, including a laser diode, a photodetector and intervening collimating and focusing optics, all of which are known in the art and not illustrated. These elements combine to form a viewing volume 58 intersecting the path traveled by the air stream.

From optical detector assembly 56, the air is drawn through a critical orifice 60 that controls the flow rate. Then, the air proceeds through a tubing section 62 to a junction with a tubing section 64, to an intake port 66 of a vacuum pump 68.

The vacuum pump also provides a purge air flow through particle counter 16. More particularly, purge air is drawn through a filter 70 located near the top of a cabinet (not shown) of the particle counter. From the filter, purge air proceeds through a tubing section 72, a critical orifice 74 that sets the purge air flow rate, a tubing section 76 and into a three way valve 78. From the valve, purge air flows through a tubing section 80 to a heat sink 82, which forms a back panel of the cabinet. Copper shredding 84, within the heat sink, enhances transfer of heat from the cabinet. Air from the heat sink travels through tubing section 64 to the inlet port of vacuum pump 68.

The vacuum pump also is used to periodically evacuate water that accumulates in reservoir 28. A tubing section 86, connected between valve 78 and condenser 34, places the valve in fluid communication with horizontal passageway 46 when the valve is actuated. Valve 78 is a solenoid valve, controlled by a timing device 88 that periodically supplies the power necessary to actuate the valve.

Whenever the solenoid valve is actuated, reservoir 28 is placed in fluid communication with vacuum pump 68, in particular through capillary tube 48, passageway 46, tubing section 86, valve 78, tubing section 80, heat sink 82, and tubing section 64. Actuation of valve 78 approximately once every five minutes, each time for about one tenth of a second, has been found satisfactory for removing accumulated water. The amount of water removed during each period of actuation is relatively small, i.e. less than one milliliter. In response to the partial vacuum created by pump 68 during evacuation, the water rapidly diffuses and evaporates, and thus is discharged at an outlet port 90 of pump 68 as water vapor within the air stream.

In general, condensation particle counter 16 operates in the manner described in connection with the counter disclosed in the aforementioned Keady patent. According to the present invention, however, particle counter 16 further incorporates a water-immiscible working fluid, and means for separating and removing water formed in condenser 34 due to the presence of water vapor in the air stream being monitored. Air enters saturation chamber 24 at inlet 26, and becomes saturated with working fluid vapor as it travels along the chamber. A deflector 91 tends to even the flow. Saturation block 22 is heated above ambient, e.g. to about 32° C., to encourage saturation. As it exits the chamber, the air is directed upwardly along bottom surface 38 of the condenser, and into fluid passages 36. As the air travels upwardly through these passages, it is cooled below the supersaturation point of the working fluid, and also below the supersaturation point of water vapor, e.g. to a temperature of about 7° C., causing both vapors to condense. It should be noted that the term "point" rather than "temperature" is used, in view of the fact that the supersaturation temperature depends on the pressure within the air stream as it travels upwardly through condenser 34.

As the air stream is cooled below the working fluid supersaturation point, working fluid condenses onto particles in the air stream, to form aerosol droplets substantially larger than the particles themselves. More particularly, particles as small as approximately 0.02 micrometers "grow" into droplets in the range of from about five to ten micrometers. Particle concentration is sufficiently low to insure a one to one correspondence of droplets to particles. Because of the substantially increased diameters, the droplets are readily detected as they pass through viewing volume 58 of the optical assembly.

Working fluid vapor also condenses onto the exposed cooling surface of the condenser, particularly the interior surfaces of passages 36, forming droplets of working fluid condensate.

Working fluid vapor condenses onto virtually all of the particles. Due to the low vapor diffusivity of the working fluid as compared to the thermal diffusivity of air, the air stream cools more quickly than the working fluid vapor diffuses to the cooling surfaces, resulting in condensation on the particles. Water, by contrast, has a vapor diffusivity greater than the thermal diffusivity of air. Consequently, virtually all of the water vapor in the air stream condenses onto the cooling surfaces of the condenser, forming water droplets on those surfaces.

Given the steep incline of the passages and their interior surfaces, water droplets and working fluid droplets tend to travel downwardly by gravity against the upward flow of air, to bottom surface 38, to projection 44, then downwardly along the exterior surface of capillary tube 48 to the collection reservoir. When the working fluid condensate reaches the bottom of the reservoir, it enters the porous saturation block and continues to descend until reaching the level of working fluid within reservoir 18. Water, however, is not accepted into the saturation block which, as previously mentioned, is formed of a hydrophobic material. Rather, the water accumulates in the reservoir, typically forming a bead as indicated in broken lines at 92 in FIG. 5. Thus, saturation block 22 performs a dual purpose, first in drawing working fluid to the periphery of saturation chamber 24 for entrainment by air drawn through the chamber, and secondly by allowing working fluid condensate to return to the pool of working fluid while preventing the water from doing so, thus to separate the water from the working fluid.

If allowed to accumulate indefinitely, water would eventually spread beyond reservoir 28 to chamber 24, interfering with and perhaps even cutting off the flow of air through the chamber. Accordingly, water is periodically evacuated from the chamber by actuating valve 78 as previously described. Thus capillary tube 48 serves a dual purpose of enhancing the downward flow of water droplets and working fluid droplets into reservoir 28, and providing (through its interior) part of the path for evacuating water.

Valve 78 could conceivably be actuated on other than a periodic basis, for example in response to a means for sensing the level of water in reservoir 28. However, a periodic evacuation of the reservoir is the preferred approach due to its relative simplicity and reliability, and further from the fact that actuation of the valve, even when reservoir 28 is empty, presents no risk of injury to the instrument.

Thus in accordance with the present invention, a water-immiscible fluid is employed in a condensation particle counter, and a hydrophobic body forming a reservoir is employed to separate water from the working fluid condensate by collecting only water in the reservoir, for periodic evacuation from the particle counter. Water is not permitted to accumulate within the device, nor does it dilute the working fluid or otherwise circulate within the device. As a result, the condensation particle counter is able to monitor particle-laden air or other gas for longer periods of time without working fluid replacement or other maintenance, even in high humidity environments.

What is claimed is:

1. A continuous flow condensation apparatus for detecting fine particles in a gas stream, including:
   a moving means for drawing a sample gas in a stream along a path, said sample gas containing fine particles and water vapor;
   a fluid source of a working fluid in which water is substantially immiscible, said working fluid being in liquid form;
   a saturation means along the path and in fluid communication with the fluid source, for providing the working 11 fluid to the gas stream for entrainment into the stream as a working fluid vapor;
   a cooling means, disposed along the path downstream of the saturation means and having a cooling surface exposed to the gas stream, for cooling the gas below the supersaturation points of the fluid vapor and the water vapor, thereby causing the fluid vapor to condense onto the particles to form aerosol droplets, and further forming working fluid condensate and water on said cooling surface;
   a sensing means downstream of the cooling means and defining a viewing volume intersecting said path, for detecting the droplets carried by the sample gas through the viewing volume; and
   a separating means proximate the condenser, for receiving the working fluid condensate and the water from the cooling surface, and returning the working fluid condensate to the fluid source while retaining the water to prevent the water from reaching the fluid source.

2. The apparatus of claim 1 further including:
   a collecting means for gathering the water retained by the separating means, and an evacuation means in fluid communication with the collecting means, for removing the water gathered by the collecting means.

3. The apparatus of claim 2 wherein:
   said separating means includes a porous structure formed of a hydrophobic material.

4. The apparatus of claim 3 wherein:
   said path along the cooling means is substantially vertical, and the separating structure is disposed directly below the cooling means.

5. The apparatus of claim 3 wherein:
   said separating structure is formed of porous, molded polyethylene.

6. The apparatus of claim 5 wherein:
   the polyethylene is impregnated with carbon.

7. The apparatus of claim 4 wherein:
   the collecting means includes a depression formed in the separating structure and open to the top of the separating structure.

8. The apparatus of claim 7 wherein:
   the depression is formed in the shape of a downwardly converging cone.

9. The apparatus of claim 7 wherein:
   a bottom portion of said cooling surface is inclined gradually downwardly and inwardly to a relatively steep downward projection at the bottom of the cooling means and centered over the depression.

10. The apparatus of claim 9 wherein:
    the path along the cooling means includes multiple fluid passages extended upwardly through the cooling means from the bottom portion of the cooling surface and converging to a common region near the top of the cooling means.

11. The apparatus of claim 9 wherein:
    the collecting means further includes an elongate tube extended vertically from the projection into the depression.

12. The apparatus of claim 11 wherein:
    the tube includes an elongate passageway open to the depression.

13. The apparatus of claim 12 wherein:
    the moving means comprises a vacuum pump, and the evacuation means includes a valve selectively operable to place the vacuum pump in fluid communication with the elongate passageway.

14. The apparatus of claim 3 wherein:
    said fluid source comprises a reservoir containing the working fluid in liquid form.

15. The apparatus of claim 14 wherein:
    the working fluid is a perfluorocarbon hydrocarbon fluid.

16. The apparatus of claim 14 wherein:
    the saturation means includes a porous saturation body disposed in the reservoir and partially submerged in the working fluid.

17. The apparatus of claim 16 wherein:
    the saturation structure and the separating structure comprise different regions of a unitary body.

18. The apparatus of claim 13 further including:
    a control means for selectively actuating the valve.

19. A continuous flow condensation nucleus counter, including:
    a means for drawing a particle-laden and water vapor containing gas along a path;
    a source containing a working fluid in which water is substantially immiscible, said working fluid being in liquid form;
    a saturation means along the path and in fluid communication with the source, for providing the working fluid to the gas stream for entrainment into the stream as a working fluid vapor;
    a cooling means, disposed along the path downstream of the saturation means and having a cooling surface exposed to the gas stream, for cooling the gas below the super-saturation point of the fluid vapor and below the super-saturation point of water vapor, thereby causing the fluid vapor to condense onto the particles to form aerosol droplets, and further forming working fluid condensate and water on said cooling surface;
    a sensing means downstream of the cooling means and defining a viewing volume intersecting said path, for detecting the droplets carried by the sample gas through the viewing volume; and
    a means proximate the condenser for receiving the working fluid condensate and the water from the cooling surface, and returning the working fluid condensate to the source while preventing the water from reaching the fluid source.

20. A process for detecting fine particles in a gas stream, including the steps of:
   directing a stream of a gas containing water vapor through a saturation means to substantially saturate the gas with a working fluid;
   directing the gas stream past a condenser, supersaturating the working fluid and the water vapor to cause the working fluid to condense onto each of the particles, to form a condensate of the working fluid along a condensing surface of the condenser, and to form water along the condensing surface;
   collecting the working fluid condensate and the water at a designated collection area;
   returning the working fluid from the collection area to the saturation means, while retaining the water to prevent it from reaching the saturation means.

21. The process of claim 20 including the further step of:
   periodically evacuating the water from the collection area.

* * * * *

UNITED STATES PATENT AND TRADEMARK OFFICE
CERTIFICATE OF CORRECTION

PATENT NO. : 5,118,959

DATED : June 2, 1992

INVENTOR(S) : Robert Caldow and Veryl L. Denler

It is certified that error appears in the above-identified patent and that said Letters Patent is hereby corrected as shown below:

Column 7, Claim 1, Line 25 "11" should be deleted.

Signed and Sealed this

Twentieth Day of July, 1993

*Attest:*

MICHAEL K. KIRK

*Attesting Officer*     *Acting Commissioner of Patents and Trademarks*